United States Patent
Tseng et al.

(10) Patent No.: US 7,057,070 B1
(45) Date of Patent: Jun. 6, 2006

(54) METHOD OF PREPARING QUATERNARY AMMONIUM HYDROXIDE AND QUATERNARY AMMONIUM CARBONATE IN AN AMINOALCOHOL SOLVENT

(75) Inventors: Chuen-Ing Tseng, Lawrenceville, NJ (US); Leigh E. Walker, Macungie, PA (US)

(73) Assignee: Lonza Inc., Annandale, NJ (US)

( * ) Notice: Subject to any disclaimer, the term of this patent is extended or adjusted under 35 U.S.C. 154(b) by 0 days.

(21) Appl. No.: 10/705,215

(22) Filed: Nov. 7, 2003

Related U.S. Application Data

(60) Provisional application No. 60/424,476, filed on Nov. 7, 2002.

(51) Int. Cl.
*C17C 211/00* (2006.01)

(52) U.S. Cl. ...................................... 564/282; 564/281

(58) Field of Classification Search ................ 564/282, 564/281

See application file for complete search history.

(56) References Cited

U.S. PATENT DOCUMENTS 5,523,487 A    6/1996   Walker
5,760,088 A *  6/1998   Walker ...................... 514/642

* cited by examiner

*Primary Examiner*—Johann Richter
*Assistant Examiner*—Chukwuma Nwaonicha
(74) *Attorney, Agent, or Firm*—Darby & Darby

(57) ABSTRACT

This invention provides a method of preparing a quaternary ammonium hydroxide compound having the formula $(NR^1R^2R^3R^4)OH$, wherein $R^1$ and $R^2$ are independently $C_1$–$C_4$ alkyl; $R^3$ is benzyl or a $C_1$–$C_{20}$ alkyl or a $C_1$–$C_{20}$ aryl-sutstituted alkyl; $R^4$ is a $C_8$–$C_{20}$ alkyl. The method includes the step of reacting a quaternary ammonium compound having the formula $(NR^1R^2R^3R^4)^+X^-$, wherein $R^1$, $R^2$, $R^3$, and $R^4$ are as defined above and X is Br or Cl, with a metal hydroxide in an aminoalcohol solvent to yield the quaternary ammonium hydroxide. The reaction forms metal bromide and/or metal chloride as a byproduct. The metal byproducts and excess metal hydroxide (if any) can be removed by methods known in the art. According to one preferred embodiment, the reaction of the quaternary ammonium compound with the metal hydroxide is performed in an anhydrous environment (i.e., with no water present).

16 Claims, No Drawings

METHOD OF PREPARING QUATERNARY AMMONIUM HYDROXIDE AND QUATERNARY AMMONIUM CARBONATE IN AN AMINOALCOHOL SOLVENT

This application claims the benefit of U.S. Provisional Application No. 60/424,476, filed Nov. 7, 2002, which is hereby incorporated by reference.

FIELD OF THE INVENTION

This invention relates to a method of preparing quaternary ammonium hydroxides quaternary ammonium carbonates, and/or quaternary ammonium bicarbonates in an aminoalcohol solvent from a corresponding quaternary ammonium chloride.

BACKGROUND OF THE INVENTION

U.S. Pat. Nos. 5,760,088 and 5,523,487 disclose the use of various quaternary ammonium hydroxides and carbonates as wood preservatives and methods for their preparation. In particular, U.S. Pat. No. 5,760,088 teaches that $C_1$–$C_{20}$ alkyl or aryl-substituted alkyl, $C_8$–$C_{20}$ alkyl quaternary ammonium hydroxides can be prepared by reacting the corresponding quaternary ammonium chloride in a solvent comprising a $C_1$–$C_4$ normal alcohol.

U.S. Pat. No. 5,523,487 discloses the reaction of a $C_1$–$C_{20}$ alkyl or aryl-substituted alkyl, $C_8$–$C_{20}$ alkyl quaternary ammonium hydroxide with carbon dioxide to form a quaternary ammonium carbonate.

Ammoniacol copper quats (ACQs) are frequently used as wood preservatives. The "quat" (i.e., quaternary ammonium compound) is typically a quaternary ammonium chloride such as didecyldimethyl ammonium chloride (DDAC) or an alkyldimethylbenzyl ammonium chloride (ADBAC). Chloride quats, however, have recently been found to corrode wood treating equipment.

SUMMARY OF THE INVENTION

This invention provides a method of preparing a quaternary ammonium hydroxide compound having the formula $(NR^1R^2R^3R^4)OH$, wherein $R^1$ and $R^2$ are independently $C_1$–$C_4$ alkyl; $R^3$ is benzyl or a $C_1$–$C_{20}$ alkyl or a $C_1$–$C_{20}$ aryl-sutstituted alkyl; $R^4$ is a $C_8$–$C_{20}$ alkyl. The quaternary ammonium compounds may be, for example, didecyl dimethyl ammonium chloride, lauryl dimethyl benzyl ammonium chloride, or coco dimethyl benzyl ammonium chloride. The method includes the step of reacting a quaternary ammonium compound having the formula $(NR^1R^2R^1R^4)^+X^-$, wherein $R^1$, $R^2$, $R^3$, and $R^4$ are as defined above and X is Br or Cl, with a metal hydroxide in an aminoalcohol solvent to yield the quaternary ammonium hydroxide. The reaction forms metal bromide and/or metal chloride as a byproduct. For example, if the metal hydroxide is potassium hydroxide and X is Cl, potassium chloride would precipitate out of the reaction mixture. The metal byproducts and excess metal hydroxide (if any) can be removed by methods known in the art, such as filtration. According to one preferred embodiment, the reaction of the quaternary ammonium compound with the metal hydroxide is performed in an anhydrous environment (i.e., with no water present).

Generally, the molar ratio of metal hydroxide to quaternary ammonium compound ranges from about 0.8 to 1.0 to about 1.5 to 1.0 (i.e., from 0.8:1.5 to 1.0:1.0). According to one preferred embodiment, the reaction mixture contains a molar equivalent or slightly less of metal hydroxide to quaternary ammonium compound (e.g., a molar ratio of 0.9–1.0 to 1.0–1.05 (i.e., 0.9:1.05 to 1.0:1.0) and more preferably a molar ratio of 1:1).

Generally, the mixture of metal hydroxide to quaternary ammonium compound contains from about 30 to about 70% by weight of solvent (based on 100% total weight of mixture) and preferably from about 40 to about 60% by weight of solvent. According to a more preferred embodiment, the mixture contains about 50% by weight of solvent. The mixture may be formed by mixing the quaternary ammonium compound, metal hydroxide (either as a solid or dissolved in a liquid), and solvent. Typically, the mixture is prepared by mixing a first solution containing the quaternary ammonium compound and a second solution in which the metal hydroxide is dissolved. The quaternary ammonium compound in the first solution may be dissolved in a solvent, such as a $C_1$–$C_4$ normal alcohol (e.g., ethanol). The solvent in the second solution may be, for example, an aminoalcohol and/or an alcohol. Preferably, both the first and second solutions are anhydrous.

Generally, the reaction is performed at ambient temperature and atmosphereic pressure with stirring.

According to a preferred embodiment, $R^3$ is benzyl or a $C_1$–$C_{20}$ alkyl. When $R^3$ is benzyl, $R^4$ is preferably a $C_8$–$C_{18}$ alkyl.

According to another preferred embodiment, $R^1$ and $R^2$ are methyl, and $R^3$ is benzyl.

Preferably, $R^4$ is a $C_8$–$C_{12}$ alkyl.

According to yet another preferred embodiment, $R^1$ and $R^2$ are methyl and $R^3$ and $R^4$ are $C_8$–$C_{12}$ alkyl.

According to yet another preferred embodiment, $R^3$ and $R^4$ are decyl.

The present invention also provides a method of preparing a quaternary ammonium carbonate having the formula $(NR^1R^2R^3R^4)_2CO_3$, wherein $R^1$, $R^2$, $R^3$, and $R^4$ are as defined above. The method includes the (a) reacting a quaternary ammonium compound having the formula $(NR^1R^2R^3R^4)^+X^-$, wherein $R^1$, $R^2$, $R^3$, $R^4$, and X are as defined above, with a metal hydroxide in an aminoalcohol solvent to yield a quaternary ammonium hydroxide having the formula $(NR^1R^2R^3R^4)OH$; and (b) reacting the quaternary ammonium hydroxide with a carbonate or bicarbonate source (such as metal carbonates (e.g., copper carbonate) and/or carbon dioxide (e.g., dry ice)). Preferably, step (b) is performed in a solvent comprising an aminoalcohol solvent and more preferably the aminoalcohol solvent used in step (a). Preferably, step (b) is performed in an anhydrous environment.

DETAILED DESCRIPTION OF THE INVENTION

Definitions

As used herein, the term "alkyl" refers to a straight or branched chain hydrocarbon group having from 1 to 4 carbon atoms, preferably from 1 to 3 carbon atoms. Suitable alkyl groups include, but are not limited to, methyl, ethyl, n-propyl, isopropyl, n-butyl, sec-butyl, and tert-butyl. Preferably, the alkyl group is straight (i.e., normal).

As used herein the term "aryl" refers to a closed carbocyclic ring structure having from 6 to 12 carbon atoms. The aryl group may be a monocyclic aryl group or bicyclic aryl group. As used herein the term "monocyclic aryl" refers to a closed aromatic carbocyclic ring structure having from 6 to 8 carbon atoms. An example of a monocyclic aryl group is phenyl. As used herein, the term "bicyclic aryl" refers to a closed bi-carbocyclic ring structure having from 9 to 12 carbon atoms. "Bicyclic aryl" encompasses the case wherein one ring of a bi-carbocyclic ring structure is saturated and the other ring is unsaturated or partially saturated and the case wherein both rings are saturated. Examples of bicyclic aryl groups include, without limitation, naphthyl.

The term "aminoalcohol" refers to a substituted or unsubstituted (hydroxyalkyl)amine. The substitutions may be on the alkyl group or the amine group. Suitable substituents include alkoxy groups. Suitable aminoalcohols include, but are not limited to, those having the formula:

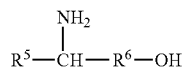

wherein $R^5$ is hydrogen or a $C_1$–$C_3$ alkyl, $R^6$ is a bond or a $C_1$–$C_3$ alkyl. According to one preferred embodiment, $R^5$ is hydrogen or a linear $C_1$–$C_3$ alkyl and $R^6$ is a linear $C_1$–$C_3$ alkyl. Preferred aminoalcohol include, but are not limited to, those having the formula $NH_2$—$(CH_2)_n$—$OH$, wherein n is an integer from 1 to 6 and more preferably 2 to 6. A more preferred aminoalcohol is ethanolamine.

Other suitable aminoalcohols include those having the formulas:

$H_{(3-n)}N(CH_2CH_2OH)_n$ where n is 1–3 (optionally substituted with one or more $C_1$–$C_5$ alkyl at one or more carbon atoms)

$H_2NCH_2CH_2(OCH_2CH_2)_nOH$ wherein n is 1–20 (optionally substituted with one or more $C_1$–$C_5$ alkyl at one or more carbon atoms)

$H_2NCH_2CH_2(NHCH_2CH_2)_nOH$ (optionally substituted with a $C_1$–$C_5$ alkyl at one or more carbon atoms)

The term "metal hydroxide" includes all known metal hydroxides. Non-limiting examples of suitable metal hydroxides are potassium hydroxide, sodium hydroxide, and mixtures thereof.

The term "carbonate or bicarbonate source" refers to sources of carbonate and bicarbonate anions, such as compounds containing the same and carbon dioxide. Suitable carbonate compounds include, but are not limited to, metal carbonates and bicarbonates. A preferred carbonate compound is copper carbonate. The metal carbonate or bicarbonate (e.g., copper carbonate) may be complexed to an aminoalcohol (e.g., ethanolamine), such as that used as the solvent in the quaternary ammonium compound/metal hydroxide reaction mixture. Another suitable carbonate or bicarbonate source is a solution containing a metal salt (such as a copper salt), which may or may not be complexed to an aminoalcohol (such as those described above), buffered with carbon dioxide. In one preferred embodiment, the carbonate or bicarbonate source is a solution of copper carbonate, copper hydroxide, and/or other copper salt complexed by ethanolamine and buffered with carbon dioxide, preferably to a pH of less than 10.5.

Other anhydrous solvents may be included in the quaternary ammonium compound/metal hydroxide reaction mixture including, but not limited to, alcohols, ketones, ethers, amines, and polyamines. Preferably, the solvent comprises from about 50 to 100% by weight of aminooalcohol (based on 100% total weight of solvent) and more preferably from about 60 to about 90% by weight of aminoalcohol. A preferred solvent includes 85–95% by weight of aminoalcohol and 5–15% ethanol.

An aminoalcohol solvent, such as those described above, may be used in the quaternary ammonium hydroxide/carbonate or bicarbonate source reaction mixture.

The method of the present invention can form aminoalcohol solutions containing a high concentration of quaternary ammonium hydroxide, carbonate, and/or bicarbonate (e.g., greater than about 20, 30, 40, 50, 60, 70, or 80% (w/w)).

The following example illustrates the invention without limitation. All parts and percentages are given by weight unless otherwise indicated.

EXAMPLE 1

Preparation of Anhydrous Alkyldimethylbenzylammonium Chloride (ADBAC)

In a 3 L reaction was charged 1208 g of lauryl dimethyl amine (($C_{12}$–$C_{16}$ alkyl)dimethylamine) (available as Barlene® 12 for Lonza Inc. of Fair Lawn, N.J., Equivalent Weight (EW)=226, 5.35 moles) and 207 g of ethanol. The reactor was purged with nitrogen gas and the contents of the reactor were heated to 60° C. Benzyl chloride (656.7 g, EW=126.6, 5.19 moles) was added to the reaction mixture over a period of 3 hours. The reaction was exothermic and the temperature was maintained at 75° C. by external cooling. The resulting solution contained 88% active ADBAC, 2% unreacted alkyldimethylamine, and 10% ethanol.

EXAMPLE 2

Preparation of Alkyldimethylbenzylammonium (ADBA) Hydroxide

In a 500 ml reaction flask was charged 27.2 g of potassium hydroxide (85% active, 0.42 moles) and 171.0 g ethanolamine. The mixture was heated to 50° C. with stirring for ½ hour. A clear, light yellow solution was obtained. To this was added 160 g of the ADBAC prepared in Example 1 at 50° C. and stirred for 12 hr. The slurry was cooled to room temperature and filtered to remove potassium chloride salt. The salt cake was washed with 10 ml of ethanolamine. ADBA hydroxide (324.5 g) was obtained as a clear, light yellow solution. Analysis (by silver nitrate titration for halide and two phase titration using sodium lauryl sulfate for the quaternary ammonium cation) indicated an ionic chloride value of 0.0918 meg/g and Quat value of 1.1792 meg/q. This represents an ion-exchange efficiency of 92.2%.

EXAMPLE 3

Preparation of Alkyldimethylbenzyl Ammonium (ADBA) Carbonate/Bicabonate

The procedure of Example 2 was repeated. ADBA hydroxide (330.5 g) was obtained as a clear, light yellow solution. Analysis indicated ionic chloride value of 0.1037 meg/g and Quat value of 1.1567 meq/g. This represents an ion-exchange efficiency of 91.0%.

To 311.3 g of the ADBA hydroxide was added 14.0 g of dry ice (by adding dry ice till 14.0 weight gain was achieved). Analysis by potentiometric pH titration indicated ADBA carbonate/bicarbonate, 43.2% activity in ethanolamine.

EXAMPLE 4

Preparation of Anhydrous Alkyldimethylbenzylammonium Chloride (ADBAC)

In a 2 L reaction flask equipped with agitator and thermometer was charged 750 g of alkyl(C12–16)dimethylamine (equivalent weight=225.8, 3.32 moles). The reactor was purged with nitrogen gas and the content of the reactor was heated to 60° C. Benzyl chloride (418.5 g, EW=126.6, 3.31 moles) was added to the reactor over a period of 3 hours. The reaction was exothermic and the temperature was maintained at 80–85° C. External cooling was applied when necessary. Analysis of the resulting product indicated 98.5% active ADBAC.

To 1000 g of the above ADBAC at 80–85° C. was added 163.0 g of ethanolamine and stirred for 1 hour. The resulting solution was a liquid at room temperature. Analysis of the resulting product indicated 84.67% ADBAC in ethanolamine.

EXAMPLE 5

Preparation of Alkyldimethylbenzylammonium (ADBA) Hydroxide

In a 500 ml reaction flask was charged 27.2 g of potassium hydroxide (85% active, 0.42 moles) and 171.0 g ethanolamine. The mixture was heated to 50° C. with stirring for 2 hours. A clear, light yellow solution was obtained. To this was added 166.5 g of the ADBAC solution prepared in Example 4 at 50° C. The mixture was allowed to stir at 50° C. overnight. The slurry was cooled to room temperature and filtered. The potassium chloride salt cake was washed with 15 ml of ethnanolamine and removed. The combined filtrate, ADBA hydroxide (321.4 g), was collected as a clear, light yellow solution. Analysis indicated an ion exchange efficiency of 90.7%.

EXAMPLE 6

Preparation of Alkyldimethylbenzyl ammonium (ADBA) Carbonate/Bicarbonate

To 310.0 g of the ADBA hydroxide was added 14.0 g of dry ice (by adding dry ice until 14.0 g weight gain was achieved). Analysis indicated ADBA carbonate/bicarbonate, 43.0% in ethanolamine.

All references cited herein are incorporated by reference. To the extent that a conflict may exist between the specification and the reference the language of the disclosure made herein controls.

What is claimed is:

1. A method of preparing a quaternary ammonium hydroxide compound having the formula $(NR^1R^2R^3R^4)OH$, wherein $R^1$ and $R^2$ are independently $C_1$–$C_4$ alkyl;

$R^3$ is benzyl or a $C_1$–$C_{20}$ alkyl or a $C_1$–$C_{20}$ aryl-sustituted alkyl;

$R^4$ is a $C_8$–$C_{20}$ alkyl, the method comprising the step of reacting a quaternary ammonium compound having the formula $(NR^1R^2R^3R^4)^+X^-$, wherein $R^1$, $R^2$, $R^3$, and $R^4$ are as defined above and X is Br or Cl, with a metal hydroxide in an aminoalcohol solvent to yield the quaternary ammonium hydroxide.

2. The method of claim 1, further comprising the step of removing any metal chloride or metal bromide formed by the reaction of the quaternary ammonium compound and the metal hydroxide.

3. The method of claim 1, where he reaction is performed in the absence of water.

4. The method of claim 1, herein any excess metal hydroxide is removed after the reaction.

5. The method of claim 1, wherein X is Cl.

6. The method of claim 1, wherein X is Br.

7. The method of claim 1, wherein $R^3$ is benzyl or a $C_1$–$C_{20}$ alkyl.

8. The method of claim 1, wherein $R^1$ and $R^2$ are methyl, and $R^3$ is benzyl.

9. The method of claim 5, wherein $R^4$ is a $C_8$–$C_{12}$ alkyl.

10. The method of claim 1, wherein $R^1$ and $R^2$ are methyl and $R^3$ and $R^4$ are $C_8$–$C_{12}$ alkyl.

11. The method of claim 1, wherein $R^3$ and $R^4$ are decyl.

12. The method of claim 1, wherein the aminoalcohol has the formula

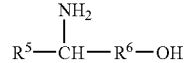

wherein $R^5$ is hydrogen or a $C_1$–$C_3$ alkyl; $R^6$ is a bond or a $C_1$–$C_3$ alkyl.

13. The method of claim 12, wherein $R^5$ is hydrogen or a linear $C_1$–$C_3$ alkyl and $R^6$ is a linear $C_1$–$C_3$ alkyl.

14. The method of claim 12, wherein the aminoalcohol has the formula $NH_2$—$(CH_2)_n$—$OH$, wherein n is an integer from 2 to 6.

15. The method of claim 12, wherein the aminoalcohol is ethanolamine.

16. A method of preparing a quaternary ammonium carbonate having the formula $(NR^1R^2R^3\ R^4)_2CO_3$, wherein $R^1$ and $R^2$ are independently $C_1$–$C_4$ alkyl;

$R^3$ is a $C_1$–$C_{20}$ alkyl or a $C_1$–$C_{20}$ aryl-substituted alkyl;

$R^4$ is a $C_8$–$C_{20}$ alkyl, the method comprising the steps of:

(a) reacting a quaternary ammonium compound having the formula $(NR^1R^2R^3R^4)^+X^-$, wherein $R^1$, $R^2$, $R^3$, and $R^4$ are as defined above and X is Br or Cl, with a metal hydroxide in an aminoalcohol solvent to yield a quaternary ammonium hydroxide having the formula $(NR^1R^2R^3R^4)OH$; and (b) reacting the quaternary ammonium hydroxide with a carbonate or bicarbonate source to yield the quaternary ammonium carbonate.

* * * * *